(12) United States Patent
Haun et al.

(10) Patent No.: US 10,485,679 B2
(45) Date of Patent: Nov. 26, 2019

(54) PROSTHETIC EXTERNAL FIXATION ASSEMBLY FOR POST-AMPUTEE AMBULATION

(71) Applicants: Dennis G. Haun, Fallston, MD (US); Johnnie Loveday, Fallston, MD (US); Christopher Bibbo, Baltimore, MD (US)

(72) Inventors: Dennis G. Haun, Fallston, MD (US); Johnnie Loveday, Fallston, MD (US); Christopher Bibbo, Baltimore, MD (US)

(73) Assignee: Post-Op Innovations, Inc., Fallston, MD (US)

( * ) Notice: Subject to any disclaimer, the term of this patent is extended or adjusted under 35 U.S.C. 154(b) by 0 days.

(21) Appl. No.: 15/961,166

(22) Filed: Apr. 24, 2018

(65) Prior Publication Data
US 2018/0303635 A1   Oct. 25, 2018

Related U.S. Application Data

(60) Provisional application No. 62/489,122, filed on Apr. 24, 2017.

(51) Int. Cl.
*A61F 2/60* (2006.01)
*A61F 2/76* (2006.01)
(Continued)

(52) U.S. Cl.
CPC .............. *A61F 2/60* (2013.01); *A61B 17/62* (2013.01); *A61F 2/76* (2013.01); *A61B 17/6425* (2013.01)

(58) Field of Classification Search
CPC ..... A61F 2/60; A61F 2/78; A61F 2/80; A61B 17/60; A61B 17/62; A61B 17/64; A61B 17/645
See application file for complete search history.

(56) References Cited

U.S. PATENT DOCUMENTS 7,306,601 B2   12/2007   McGrath
8,192,434 B2    6/2012   Huebner et al.
(Continued)

OTHER PUBLICATIONS

Lam, A., Garrison, G. and Rozbruch, SR, Lengthening of Tibia after Trans-Tibial Amputation: Use of a Weight Bearing External Fixator-Prosthesis Composite, HSS J. Feb. 2016;12(1):85-90. doi: 10.1007/s11420-015-9463-7. Epub Sep. 8, 2015.

*Primary Examiner* — Julianna N Harvey
*Assistant Examiner* — Christina Negrellirodriguez
(74) *Attorney, Agent, or Firm* — Royal W. Craig; Gordon Feinblatt LLC

(57) ABSTRACT

A fixation assembly for attaching a prosthetic leg and foot combination directly to an external ring fixation assembly via a protective socket, and yet allow full adjustment of length and offset, protection of the residual stump when in use, and quick-disconnect of the socket when not in use. The device is meant for use with any existing external fixation ring assembly for fixation to a femur or tibia, and any prosthetic leg/foot combination. The fixation assembly generally includes a molded concave socket having a mounting base at its apex for mounting the prosthetic leg/foot, an articulating ring adjustably attached to the socket, and a plurality of struts there between. Each strut has a first locking pivot joint at one end pivotally attached to the articulating ring and a second locking pivot joint at an opposing end pivotally attached to the rim of the socket. The articulating ring is removably attached to the external ring fixation assembly by a plurality of detent pins for releasable attachment.

7 Claims, 4 Drawing Sheets

(51) Int. Cl.
*A61B 17/62* (2006.01)
*A61B 17/64* (2006.01)

(56) References Cited

U.S. PATENT DOCUMENTS

| | | |
|---|---|---|
| 8,252,066 B2 | 8/2012 | Haun |
| 8,323,282 B2 | 12/2012 | Taylor |
| 9,301,859 B2 | 4/2016 | Haun |
| 9,381,129 B1 | 7/2016 | Vicik |
| 2014/0121783 A1* | 5/2014 | Alley ................ A61F 2/76 623/33 |
| 2015/0112339 A1 | 4/2015 | Lindahl et al. |

* cited by examiner

PROSTHETIC EXTERNAL FIXATION ASSEMBLY FOR POST-AMPUTEE AMBULATION

CROSS-REFERENCE TO RELATED APPLICATION(S)

The present application derives priority from U.S. provisional application Ser. No. 62/489,122 filed Apr. 24, 2017.

BACKGROUND OF THE INVENTION

1. Field of the Invention

The present invention relates generally to prosthetics and more particularly, to a prosthetic leg mounting system for external ring fixators for faster post-operative ambulation.

2. Description of the Background

When a patient encounters a traumatic injury to his or her lower limb, external ring fixators are often used as a method of immobilizing leg and other limb bones to allow a fracture to heal. They utilize two or more rings with radial pins or screws that are placed into the bone on all sides of the fracture. As the bones mend back together, the external fixator can be adjusted such that the bones remain in an optimal positions during the healing process.

For example, U.S. Pat. No. 7,306,601 to McGrath et al. (Quantum Medical Concepts, Inc.) issued Dec. 11, 2007 shows a typical external ring fixation system.

It is also known that the healing process can be accelerated by getting the patient up and moving to increase circulation, which helps with healing. For this reason some patients have an additional ring, or footplate, attached beneath their foot that allows them to bear weight and ambulate. This additional ring or foot ring typically attaches with four (or more) threaded rods that are secured with multiple nuts above and below each ring.

For example, U.S. Patent Application 20150112339 by Lindahl et al. (Aalto University Foundation) published Apr. 23, 2015 shows an external ring fixator with attached shoe for controlling ankle movement.

U.S. Pat. No. 8,192,434 to Huebner et al. (Quantum Medical Concepts LLC) issued Jun. 5, 2012 shows an external ring fixation assembly with a foot-supporting plate.

U.S. Pat. No. 8,323,282 to Taylor issued Dec. 4, 2012 shows a walking plate for an orthopedic ring-fixator.

U.S. Pat. No. 9,381,129 to Vicik issued Jul. 5, 2016 (MGV Enterprises, Inc) shows an external ring-fixator and auxiliary support having a quick-release mechanism.

For the very same reasons, it is likewise desirable to get amputates ambulating as soon as possible after their procedures, but this is more difficult and less common. This is noted in the "Lengthening of Tibia . . ." article by Garrison and Rozbruch (2016) where the authors attached a prosthetic leg so a weight-bearing external ring fixator to allow for early weight bearing and exercising. In this case, the prosthesis was simply screwed to a bottom ring.

What is needed is a prosthetic external ring fixation assembly that facilitates immediate attachment of a prosthetic leg and foot for immediate post-amputee ambulation it get the patient up and moving, increase circulation, and expedite healing.

SUMMARY OF THE INVENTION

In accordance with the foregoing it is an object of the invention to provide a prosthetic leg mounting system for external ring fixators that facilitates immediate attachment of a prosthetic leg and foot for immediate post-amputee ambulation to get the patient up and moving, increase circulation, and expedite healing.

The foregoing and other objects are accomplished with an improved prosthetic external ring fixation assembly for quick-connect adjustable attachment of a prosthetic leg for immediate post-amputee ambulation. The device is configured for use with an existing external fixation ring assembly for fixation to a femur or tibia, and an existing prosthetic leg and foot combination of choice. The assembly generally includes an articulating ring adjustably-attached to a concave socket by locking-ball-joint struts, and quick-connect pins insertable through the external ring fixation assembly and into receptacles on the articulating ring for releasable attachment. The socket has an open end surrounded by a reinforcing ring, and a closed end at its apex with a mounting base for mounting the prosthetic leg/foot. The quick-connect mechanism is a plurality of detent pins that allow releasable mounting of the socket-articulating ring to the external fixation ring assembly via the reinforcing ring.

BRIEF DESCRIPTION OF THE DRAWINGS

Other objects, features, and advantages of the present invention will become more apparent from the following detailed description of the preferred embodiments and certain modifications thereof when taken together with the accompany drawings in which.

DETAILED DESCRIPTION OF THE PREFERRED EMBODIMENT

Reference will now be made in detail to preferred embodiments of the present invention, examples of which are illustrated in the accompanying drawings. Wherever possible, the same reference numbers will be used throughout the drawings to refer to the same or like parts.

The present invention is an improved prosthetic external ring fixation assembly for quick-connect adjustable attachment of a prosthetic leg post-amputee ambulation as soon as possible after their procedures.

Figure 1:
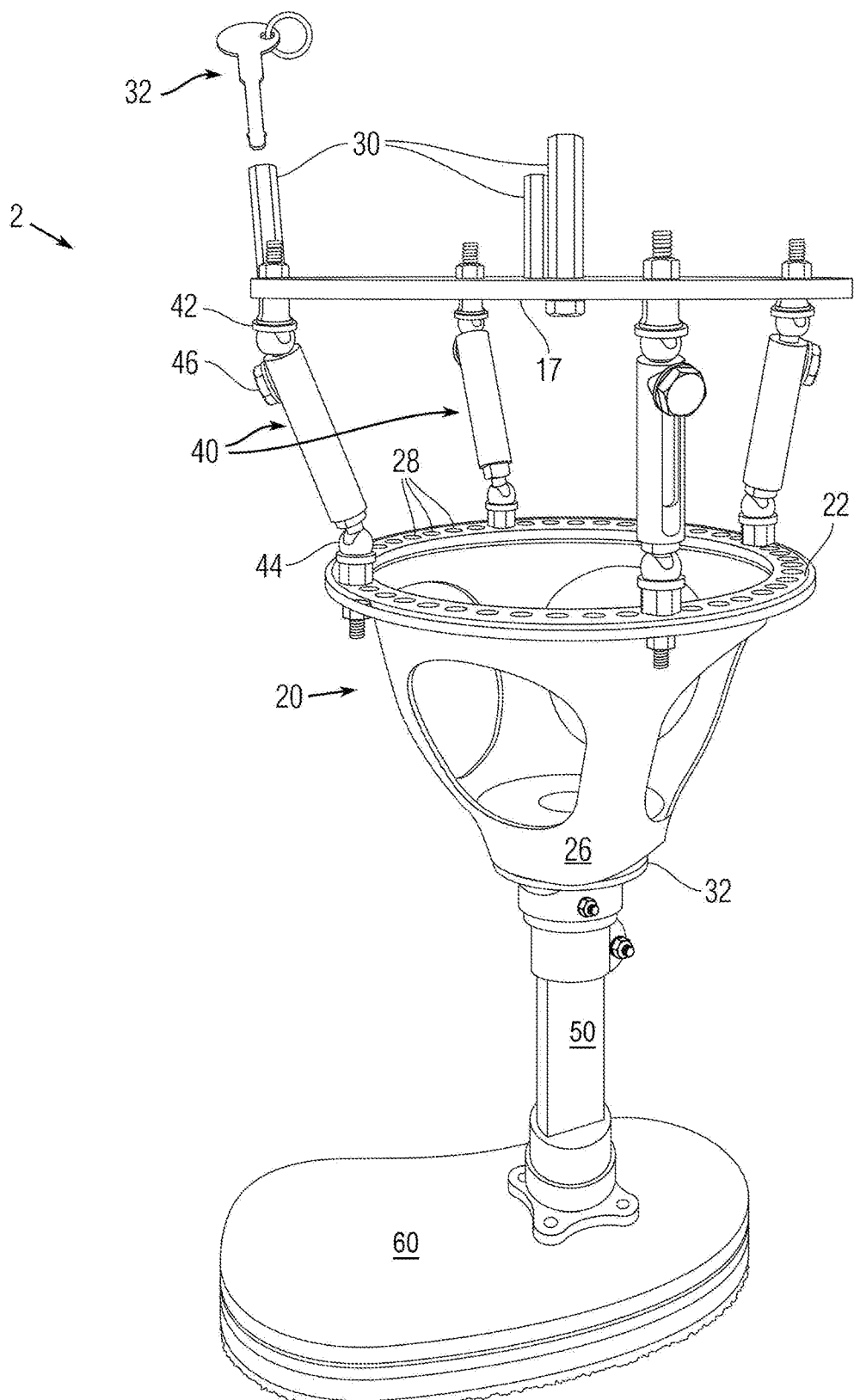
FIG. 1 is a perspective illustration of a system for mounting a prosthetic leg to an external ring fixation assembly according to the invention.
Figure 2:
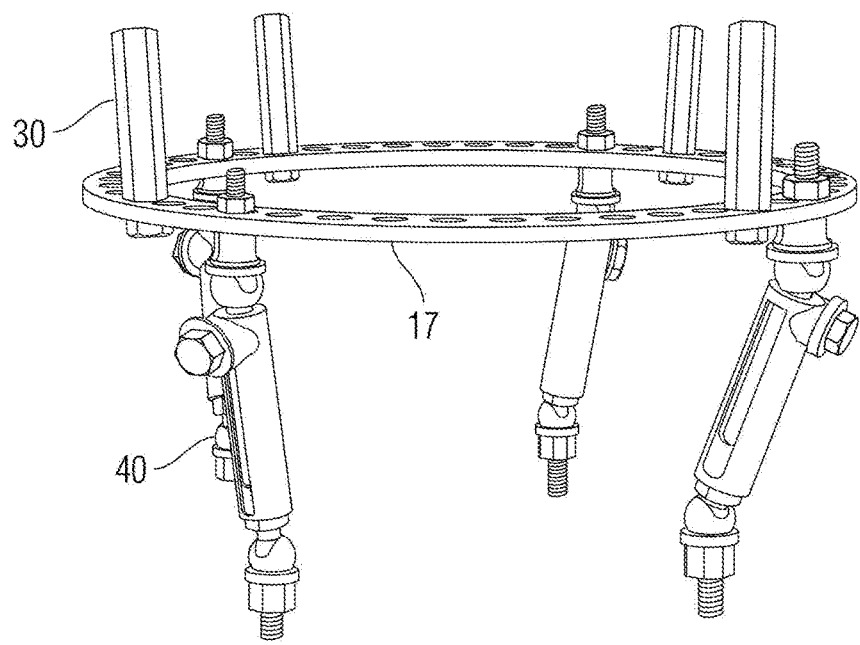
FIG. 2 is perspective exploded illustration of the system 2 of FIG. 1.
Figure 2:
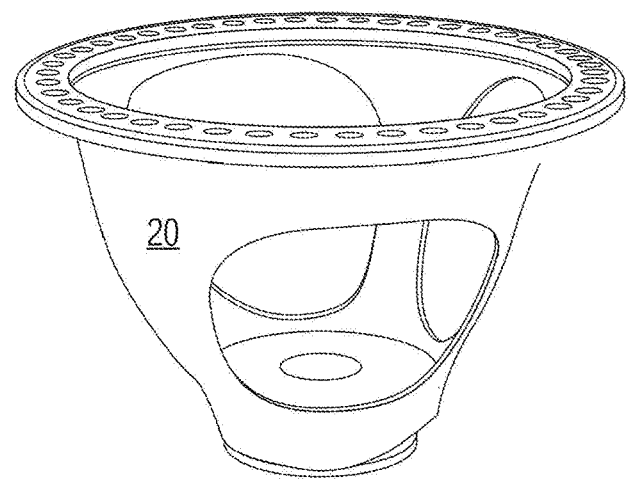
Figure 2:
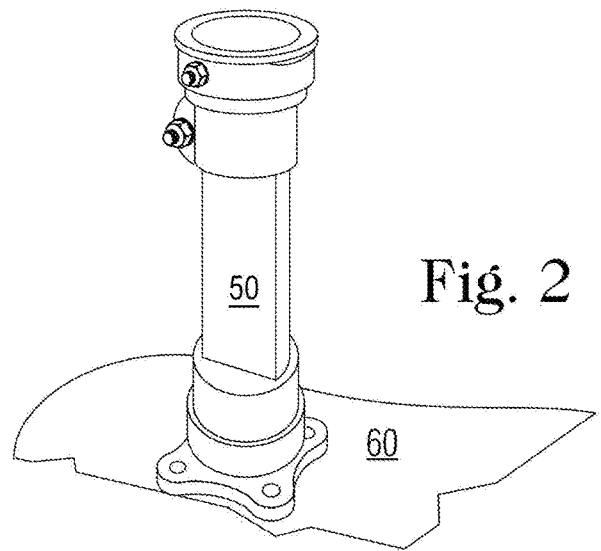
Figure 4:
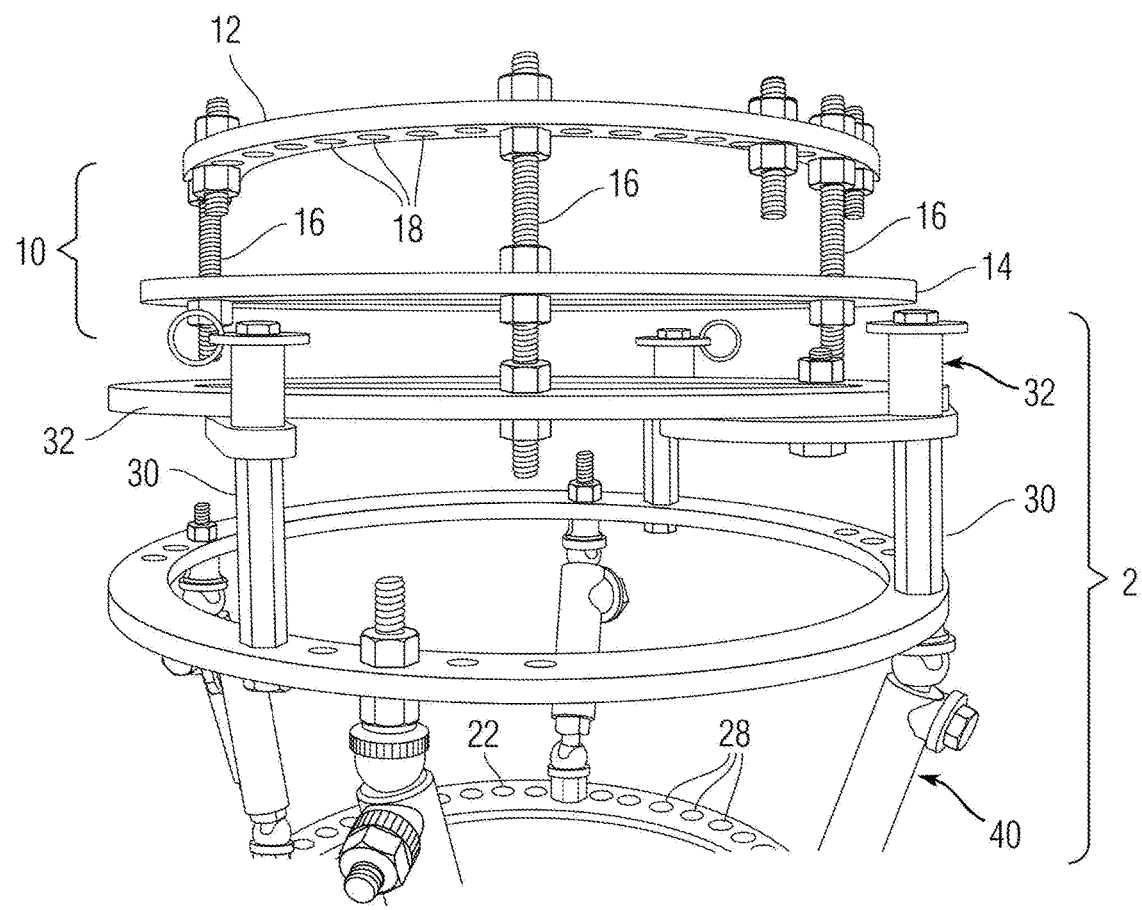
FIG. 4 is a close-up perspective illustration of the system 2 as in FIG. 3 connected to an external ring fixator 10.

FIGS. 1-2 are perspective illustrations of the system 2 for mounting a prosthetic leg to an external ring fixation assembly according to the invention. FIG. 4 shows the system 2 attached to an external ring fixation assembly 10.

The system 2 is configured for quick-release attachment to the external fixation ring assembly 10 (FIG. 4) for fixation to the thigh bone (femur) or to the tibia (stinbone). The external fixation ring assembly 10 is a conventional component used to stabilize bone and soft tissues at a distance from the operative or injury focus. The external fixation ring assembly 10 includes at least one ring, in this case two rings 12, 14 connected to one another via threaded struts 16. The struts 16 may, for example, be received in openings 18 of the rings 12, 14 and screwed thereto. The struts 16 determine the spacing and/or angular disposition of the rings 12, 14 by holding them in a substantially fixed relative disposition. The struts 16 may be arranged around the rings 12, 14 as desired, preferably at 0, 45, 90 and 135 degree equiangular increments although three to six struts may be used as a matter of design choice. Each strut 16 may be adjustable in length and/or angular disposition relative to the rings 12, 14. In some commercial embodiments, each strut 16 may have a length-adjustment capability that allows the length of the strut 16 to be adjusted telescopically (and then locked at length). The rings 12, 14 may be connected to bone in a conventional manner via any suitable pins, rods, and/or screws.

The system 2 includes a mounting assembly 20 comprising an articulating ring 17 pivotally attached to a socket 20, the articulating ring 17 being attached to the lowermost ring 14 (seen in FIG. 4) of external fixation ring assembly 10 by a plurality of spacers 30 that accept quick-connect pins 32 for removable connection on one side to the lowermost ring 14. The quick-connect pins 32 are preferably detent lock pop-and-plunger pins, and most preferably button-handle lock pins, 2", ¼" diameter.

The articulating ring 17 is attached to the socket 20 by a plurality (preferably four) unidirectional-pivoting length adjustable struts 40. Each strut 40 is pivotally-connected to the articulating ring 16 at one end by a first unidirectional pivot joint 42, and is pivotally-connected to a reinforcing ring 22 at the rim of socket 20 by a second unidirectional pivot joint 44. Each strut 40 can be independently lengthened or shortened and fixed in length and/or orientation by a locking screw 46. The struts 40 preferably include threaded distal ends for attachment, and are secured by nuts at one end in openings 18 of the lower ring 14 and screwed thereto. The struts 40 are likewise secured by nuts at the other end in openings 28 of the reinforcing ring 22 at the rim of socket 20. The struts 40 may each be a Tru-Lock™ Rapid Strut manufactured by Orthofix SRL. This configuration allows for limited spatial adjustment (position, orientation and fixation) of the articulating ring 16 (and external fixation ring assembly 10) relative to the socket 20 within a three-dimensional frame of reference.

The other side of socket 20 is configured with a prosthetic mounting plate 32. The mounting plate 32 may vary depending on the desired prosthetic. As an example, the mounting plate 32 may be a 4-hole pyramid adapter generally including a keyed male pin for docking in a conventional pyramid receptacle, the pin capable of being locked in position with set screws. The docking pin/receptacle combination further allows mounting a prosthetic leg 50 and foot 60 thereto, allowing for early weight bearing and exercising. The socket 20 also protects the residual stump post-amputation. The foot 60 may be a foreshortened prostheses ("stubby") such its shown and described in U.S. Pat. No. 9,301,859 to Haun, or any other suitable foot, and an exemplary receptacle in U.S. Pat. No. 8,252,066 to Haun or other suitable receptacle.

The foregoing system 2 is quickly attachable, fully adjustable, and allows the amputee patient to remain active and ambulatory with minimal assistive devices, improving circulation and healing as well as psychological advantages.

Figure 3:
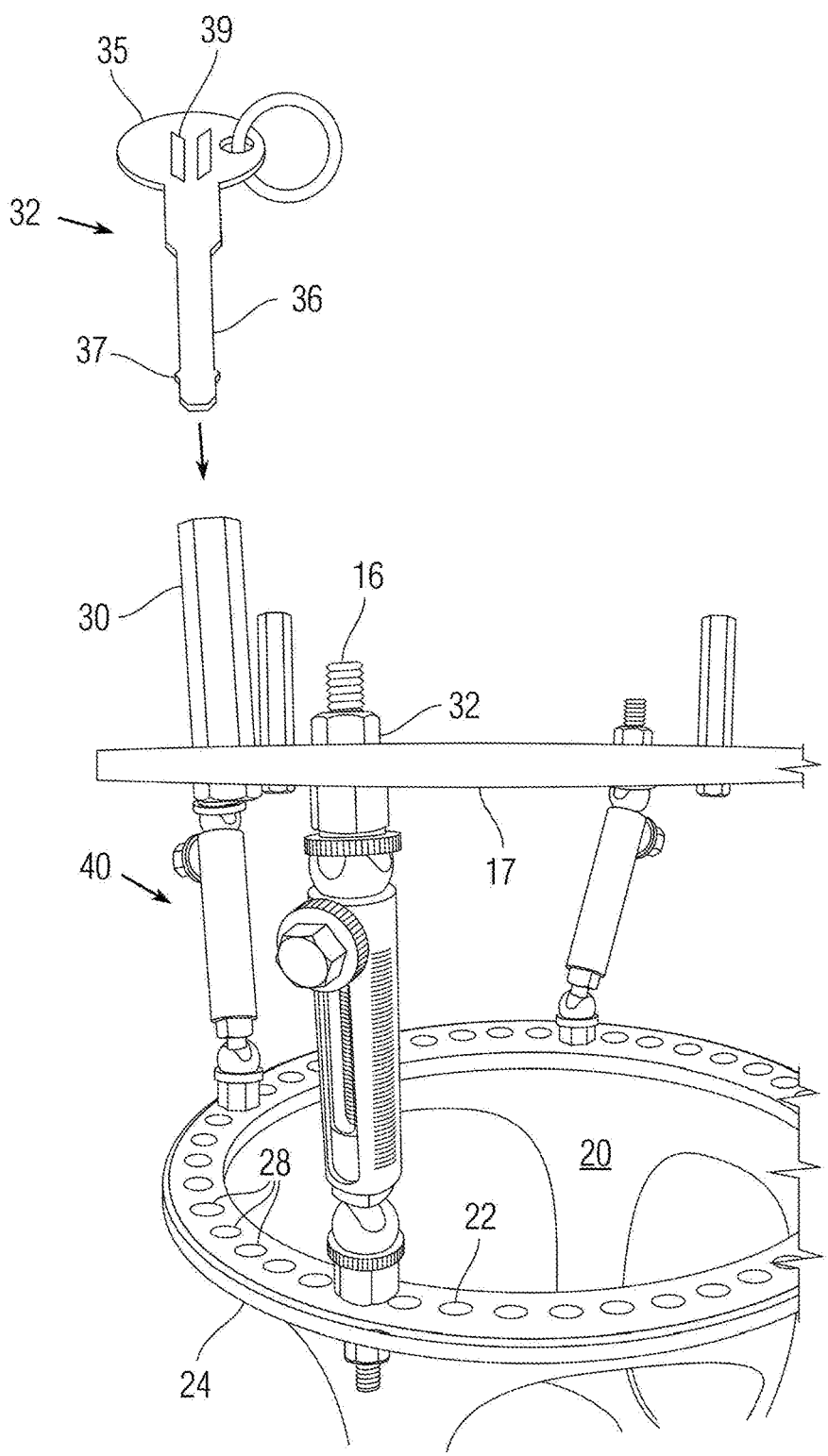
FIG. 3 is a close-up perspective illustration of the system 2 of FIGS. 1-2 adapted for quick-connect removable connection to an external ring fixator.

FIGS. 3-4 are perspective illustrations of the socket 20. The socket 20 is a shallow stump socket configured for enclosing the lower residual stump socket of an amputated limb. Toward this end socket 20 generally comprises an open concave receptacle formed of rigid lightweight plastic with a closed end and an open end surrounded by an outwardly-flared circular rim 24. The outwardly-flared circular rim 24 is recessed to seat a reinforcing ring 24, which is a circular metal (e.g., aluminum) ring defined by equal angularly-spaced mounting holes. The rim 24 is reinforced by the ring 22 which is compression-fit and/or adhered therein.

Figure 5:
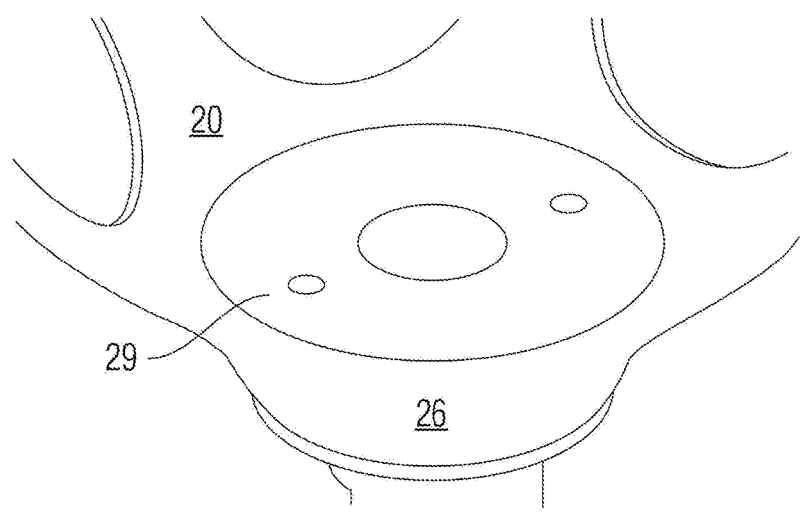
FIG. 5 is another close-up perspective illustration of the socket of FIG. 3.

The socket 20 is most preferably formed of Kevlar™ or other fiber-reinforced plastic, but may alternatively be molded from, e.g., bisphenol A (BPA) plastic. As seen in FIG. 5 the socket 20 is formed with a reinforced-thickness circular platform 26 at its apex, the platform 26 having an interior recess seating a circular silicon pad 29 for comfort and with surface features (annular ribs) for grip. The mounting base 32 for mounting prosthetic leg 50 and foot 60 is screw-attached exteriorly to the platform 26 (seen in FIG. 1). The base 32 may be any suitable prosthetic leg attachment base, such as a conventional prosthetic pyramid base adapted for attachment of a prosthetic leg 50 and foot 60 via a pyramid, receiver, as is well-known in the art.

FIG. 3 is a close-up view of a quick-connect length-adjustable spacer 30 and quick-connect pin 32. The spacer 30 may be secured on one side of articulating ring 17 by the threaded end of strut 40 screwed therein through the other side of ring 17. Alternatively, the spacers 30 may be secured by separate bolts. Each spacer 30 is a tubular spacer having an internally-threaded receptacle on one end (bottom) and an internally smooth-bore receptacle on the other end (top). The internally-threaded end of receptacle 31 is screw-attached to the articulating ring 17, and the smooth-bore receptacle on the other end (top) is detachably attached to the lowermost ring 16 of the external ring fixation assembly 10 by a detent pin 32 that passes through the smooth-barreled metal spacer 30 and is anchored therein. As sees in FIG. 3, the detent pin 32 comprises an enlarged head 35 attached to aa elongate cylindrical shaft 36. The shaft 36 terminates at a conical tip configured with a detent bearing 37. The detent bearing 37 may be released by depressing a thumb-button 39 in the head 35, thereby freeing the bearing 37 to recess inside the shaft 36, thereby allowing removal of the detent pin from spacer 30. Conversely, releasing the thumb-button locks the bearing 37 in place thereby locking the pin 32 in the spacer 30.

The distance of the socket 20 from the external fixation assembly 10 and/or the offset angle of the prosthetic foot 60 (FIG. 1) may be adjusted by adjusting the length and/or pivot angles of the unidirectional-pivoting length adjustable struts 40. After use, the entire system 2 may be quick-released and removed from the external ring fixation assembly 10 (and the patient) by removing the quick-connect pins 32.

It should now be apparent that the foregoing system 2 is quickly attachable, fully adjustable, and allows the amputee patient to remain active and ambulatory almost immediately with minimal assistive devices, improving circulation and healing as well as psychological advantages.

Those skilled in the art will understand that various modifications and variations can be made in the present invention without departing from the spirit or scope of the invention. It is to be understood, therefore, that the invention may be practiced otherwise than as specifically set forth in the appended claims.

What is claimed is:

1. An external ring fixation assembly for quick-connect adjustable attachment of a patient's prosthetic leg to an external ring fixator for immediate post-amputee ambulation, comprising:
a concave socket for protection of said patient's residual stump, said concave socket including an open end having a rim and a closed end having a prosthetic leg-mounting plate attached thereto;

an articulating ring adjustably-attached to the rim of said concave socket;

a plurality of spacers mounted around said articulating ring, each said spacer having an internal lumen;

a plurality of quick-release pins each insertable into a corresponding one of the plurality of spacers of said articulating ring; and a plurality of struts adjustably attached between said articulating ring and the rim of said socket, each of said plurality of struts having a first locking-ball-joint at one end pivotally attached to the articulating ring and a second locking-ball-joint at an opposing end pivotally attached to the rim of said socket.

2. The external ring fixation assembly according to claim 1, wherein each of said plurality of quick-release pins comprises a push-button detent mechanism.

3. The external ring fixation assembly according to claim 2, wherein each of said plurality of quick-release pins comprises a movable ball bearing actuated by said push-button detent mechanism.

4. The external ring fixation assembly according to claim 1, wherein each of said plurality of struts is length adjustable.

5. The external ring fixation assembly according to claim 4, wherein said plurality of struts comprises four struts.

6. The external ring fixation assembly according to claim 1, further comprising a circular rubber pad affixed inside the closed end of said socket.

7. The external ring fixation assembly according to claim 1, wherein said socket comprises a fiber-reinforced composite.

* * * * *